United States Patent
Fried et al.

(10) Patent No.: US 6,221,068 B1
(45) Date of Patent: Apr. 24, 2001

(54) METHOD FOR WELDING TISSUE

(75) Inventors: Nathaniel Fried, Baltimore, MD (US); Joseph T. Walsh, Jr., Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/232,352

(22) Filed: Jan. 15, 1999

Related U.S. Application Data

(60) Provisional application No. 60/071,553, filed on Jan. 15, 1998.

(51) Int. Cl.[7] .................................................. A61B 18/18
(52) U.S. Cl. ...................... 606/8; 606/3; 606/9; 606/10; 606/14; 128/898; 607/89
(58) Field of Search ...................... 606/2, 8, 9, 213–216; 600/473; 607/80–89; 128/395–398

(56) References Cited

U.S. PATENT DOCUMENTS

| | | |
|---|---|---|
| 4,633,870 | 1/1987 | Sauer . |
| 4,672,969 * | 6/1987 | Dew ....................................... 128/397 |
| 4,892,098 | 1/1990 | Sauer . |
| 5,002,051 | 3/1991 | Dew et al. . |
| 5,057,099 | 10/1991 | Rink . |
| 5,152,759 | 10/1992 | Parel et al. . |
| 5,156,613 | 10/1992 | Sawyer . |
| 5,209,776 | 5/1993 | Bass et al. . |
| 5,281,211 | 1/1994 | Parel et al. . |
| 5,290,272 | 3/1994 | Burstein et al. . |
| 5,334,191 | 8/1994 | Poppas et al. . |
| 5,354,323 | 10/1994 | Whitebook . |
| 5,409,479 * | 4/1995 | Dew et al. ................................. 606/9 |
| 5,409,481 | 4/1995 | Poppas et al. . |
| 5,498,259 | 3/1996 | Mourant et al. . |
| 5,540,677 | 7/1996 | Sinofsky . |
| 5,552,452 | 9/1996 | Khadem et al. . |
| 5,571,216 | 11/1996 | Anderson . |
| 5,582,190 | 12/1996 | Slavin et al. . |
| 5,591,157 | 1/1997 | Hennings et al. . |
| 5,611,794 * | 3/1997 | Sauer et al. ................................. 606/8 |
| 5,612,050 | 3/1997 | Rowe et al. . |
| 5,642,997 | 7/1997 | Gregg, II et al. . |
| 5,662,643 | 9/1997 | Kung et al. . |
| 5,669,934 | 9/1997 | Sawyer . |
| 5,725,522 | 3/1998 | Sinofsky . |
| 5,749,895 | 5/1998 | Sawyer et al. . |
| 5,762,609 * | 6/1998 | Benaron et al. ...................... 600/473 |
| 5,814,040 * | 9/1998 | Nelson et al. ........................... 606/9 |
| 5,824,015 * | 10/1998 | Sawyer ................................. 606/124 |
| 5,827,265 | 10/1998 | Glinsky et al. . |

* cited by examiner

*Primary Examiner*—John P. Leubecker
*Assistant Examiner*—Ahmed Farah
(74) *Attorney, Agent, or Firm*—Welsh & Katz, Ltd.

(57) ABSTRACT

Radiation is delivered to a wound in a series of sufficiently short pulses, with adequate cooling between individual pulses, to produce cumulative thermal denaturation and welding of the skin edges at the immediate area of the wound site, while avoiding unnecessary thermal damage to surrounding healthy tissue.

19 Claims, 4 Drawing Sheets

FIG. 5A  FIG. 5B

METHOD FOR WELDING TISSUE

This application claims benefit of Provisional Ser. No. 60/071,553 filed Jan. 15, 1998.

This invention is made with government support under the National Science Foundation, Grant # BES-9222483. The government has certain rights in the invention.

BACKGROUND OF THE INVENTION

This invention relates to tissue welding, more particularly, to a method by which tissue may be welded reliably under controlled conditions. Lasers of various types have long been used in various medical applications. In a wide variety of surgical techniques, laser light is used to cut tissue, and to coagulate simultaneously along the cut. Some progress has been made previously, in the use of laser energy for joining tissue, commonly termed tissue welding. The ultimate goal is to facilitate the joining of tissues with a minimum of scar tissue formation, and high tensile strength at the joined edges. Progress in the field of laser tissue welding has been slow due, in part, to the large number of laser parameters that need to be considered in the welding process. These parameters include wavelength, radiant exposure, irradiance, pulse duration, pulse repetition rate, irradiation time, spot size, dye selection, and adhesive selection. Past tissue welding studies have used a wide range of values for these welding parameters, making the interpretation of results and comparison between studies difficult.

The majority of previous tissue welding studies have used a laser operated in either continuous wave (CW) mode or quasi-CW mode with constant surface temperature control. During CW and temperature-controlled welding, heat diffuses from the weld site into surrounding healthy tissue, typically resulting in a large zone of thermal damage. A zone of thermal damage greater than ~200 $\mu$m extending laterally from the weld site may inhibit wound healing and result in excessive scarring. For some applications, such as skin welding, too much scar tissue may be clinically unacceptable even if strong welds can be achieved.

SUMMARY OF THE INVENTION

The method of the subject invention involves the use of pulsed delivery of radiation in combination with a dye, to initiate healing by producing strong welds in tissue that contain proteins, most significantly collagen, with strong adhesive properties when denatured, while limiting the thermal damage zone to the immediate area of the weld site. The radiation is delivered in pulses of short duration to achieve confinement of the temperature rise to the immediate area of the weld site. A pulse of radiation may be achieved by interrupting the radiation source or by passing radiation over the weld site. A series of multiple pulses of up to approximately 250 ms in duration are delivered to the weld site to achieve cumulative thermal denaturation over time, resulting in the formation of a weld with high tensile strength. Sufficient active or passive cooling is allowed between successive pulses to maintain the temperature in the tissue adjacent to the weld site below denaturation temperatures. A dye is applied to the tissue edges to act as a selective absorber of the radiation. The wavelength of the radiation is selected such that there is strong absorption by the dye and minimal absorption in the native tissue. Thus, heating and denaturation occur readily along the weld edges where the dye is located but not in the adjacent native tissue where absorption is minimal. The radiation is incident over a region of the surface that is sufficient for deep penetration of the radiation; thus each pulse of radiation heats a significant thickness of the weld site. Using this technique, it is possible to produce both strong welds and minimize thermal damage to surrounding healthy tissue, that would otherwise result in delayed wound healing and excessive scarring.

DETAILED DESCRIPTION OF THE INVENTION

Figure 1:
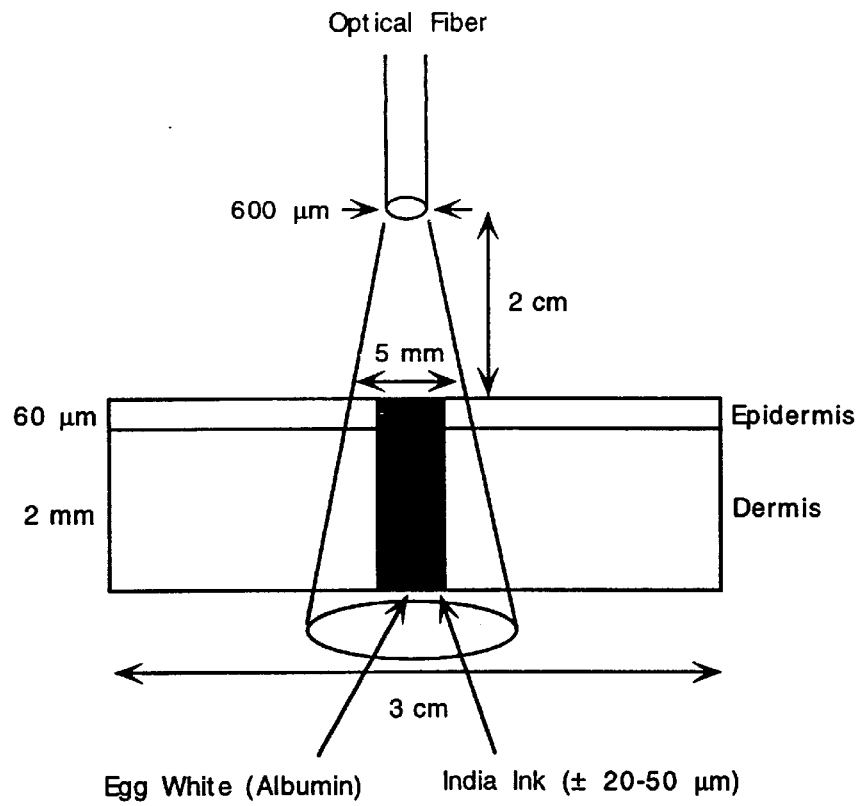
FIG. 1 is a schematic of an apparatus for the dye-assisted pulsed laser skin welding system of the subject invention.

In general, a dye is applied to the incision or wound edges, and a laser with a wavelength in the range of 450 nm to 2.1 $\mu$m, and preferably from 650 to 1300 nm, if one desires several millimeter thick welds, delivers sufficiently short pulses of radiation to confine heating to the immediate area of the weld site during the duration of the pulse and limit the temperature at the weld site to below approximately 100° C., and preferably optimally to approximately 60° C. Sufficient cooling between delivery of successive pulses of radiation is necessary to allow the temperature at the weld site to cool to approximately its initial, pre-radiation temperature and preferably to prevent thermal damage to surrounding tissue or within about 5° C. of its pre-radiation temperature. The application of multiple pulses of radiation results in cumulative thermal denaturation at the weld site, producing optimal tensile strength of the weld. A list of possible lasers that may be used in the subject invention and their respective wavelengths is provided in Table 1 below.

TABLE 1

| Lasers that may potentially be used for tissue welding and their respective wavelengths. | |
|---|---|
| Laser | Wavelength |
| Argon | 488 nm |
| Argon | 514.5 nm |
| Doubled Nd:YAG | 532 nm |
| Alexandrite | 720–800 nm |
| Ga:Al:As diode | 810 nm |
| In:Ga:As diode | 980 nm |
| Nd:YAG | 1.06 $\mu$m |
| Nd:YAG | 1.32 $\mu$m |
| Ho:YAG | 2.06 $\mu$m |

The subject invention combines the application of pulsed radiation and an exogenous absorber, such as a dye, to produce welds that are much stronger than produced using previous welding techniques, while at the same time producing less thermal damage to surrounding tissue. The welds produced pursuant to the subject invention stay closed consistently without the use of any aids such as sutures or biological adhesives. The main features of the subject invention include: (1) the heating source and the appropriate heating parameters, (2) an exogenous absorber, (3) an apposition system, and (4) a cooling system.

HEATING SOURCE

The first component of the system is the heating source and the heating parameters necessary to produce a successful weld. The heating source should have the following characteristics. It should be a source that emits radiation (e.g. in the form of optical radiation, microwaves, radio frequency waves, or sound waves) at a wavelength or frequency such that the radiation penetrates as deep as, or deeper than, the thickness of the tissue that is being welded. It is important that the radiation penetrates into the deeper layers of the tissue, so that a strong, full-thickness weld can be achieved, rather than a weak, superficial surface weld.

The radiation can be delivered using one of the following methods: directly through the open air as a 'free beam', through an optical fiber or other form of waveguide, or using an articulating arm consisting of a group of mirrors. If the radiation is delivered through a waveguide, then it may be connected to a pen handle for convenient delivery, or a microscope or other focusing optics, or part of a more elaborate system, such as an endoscope.

The radiation should be emitted either in pulsed mode or scanned across the tissue such that it produces pulses sufficiently short enough to confine the thermalized energy to the immediate area of the weld site during the duration of the pulse itself. Thermal confinement is necessary to avoid excessive thermal damage to surrounding tissue caused by heat diffusion during a single pulse of radiation. The conditions for thermal confinement are governed by thermal diffusion considerations. However, each pulse must impart sufficient energy to denature some structural protein, such as collagen. An approximate solution for the thermal relaxation time, $\tau_{Th}$, of a structure cooling by diffusion is given by Eq. (1).

$$\tau_{Th} = \frac{d^2}{4\kappa} \quad (1)$$

To limit heat diffusion from the weld site during the laser pulse, the pulse duration, $\tau_p$, must be on the order of, or less than, the thermal relaxation time, where d is the desired width of thermal denaturation, and K is the thermal diffusivity (k~1.3 ×10$^{-3}$ cm$^2$/s for skin). For example, for the application of skin welding, a 100 ms pulse duration yields an acceptable zone of thermal confinement of ~230 $\mu$m although it is anticipated that radiation pulses with durations less than approximately 120 ms will result in skin welds with acceptable thermal denaturation. Further, the length of the pulse will vary as the duration or residence of the laser spot upon the wound surface increases or decreases, and will also vary with the cooling duration.

Figure 4:
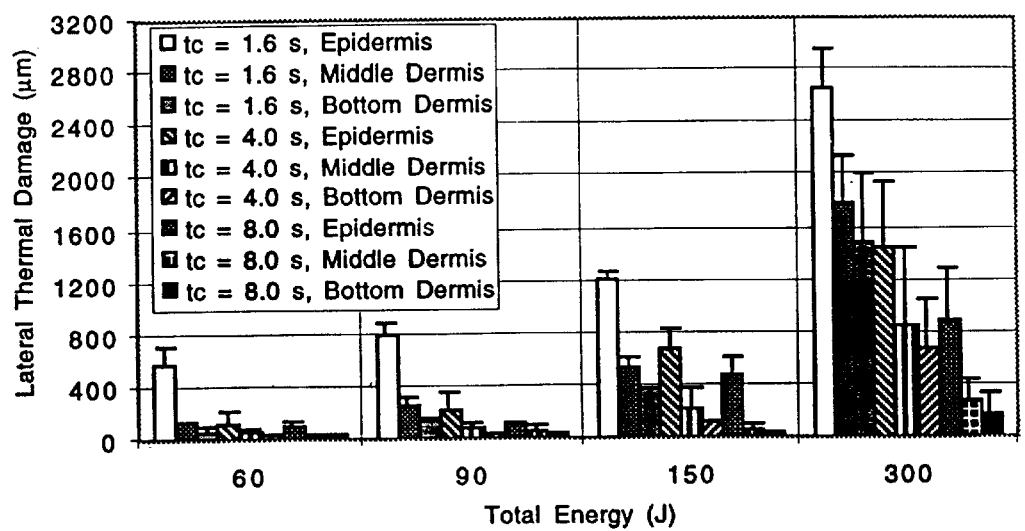
FIG. 4 is a graph showing the size of thermal damage zone as a function of total energy delivered to the wound site, inter-pulse cooling time, and location in skin.

Sufficient cooling should be allowed between successive pulses of radiation to allow the weld site to cool to approximately its initial, pre-welding temperatures or within 5° C. of such initial temperature. This is important because pulsed delivery of radiation with minimal cooling between pulses results in a buildup of the baseline temperature at the weld site over time. As successive pulses are applied to the tissue, the baseline will eventually rise above the denaturation temperature of the tissue, if insufficient cooling occurs. Such a situation would be analogous to CW welding, and result in excessive thermal damage to both the weld site and the surrounding healthy tissue. This result is shown in FIG. 4, where three different cooling durations were studied for skin welding. The cooling durations, $\tau_c$=1.6, 4.0, and 8.0 seconds, represent short, medium, and long-duration cooling between successive laser pulses, respectively. The laser beam scan velocity in one embodiment is optimally 50 mm/sec, but should at least be greater than 15 mm/sec, dependent upon spot size and laser power. It is anticipated, dependent on the cooling method, that such cooling durations will vary from 1 to 10 seconds, though the maximum cooling duration may be as long as desired. A conservative estimate for the time of temperature decay during the cooling phase, $\tau_c$, is on the order of 50–100 times the thermal relaxation time. By using suitably short pulses with sufficient cooling between pulses ($\tau_c > 100\tau_{Th}$), selective thermal damage to the weld site can be achieved without irreversibly damaging the tissue adjacent to the weld. For example, using the application of pulsed delivery of radiation to confine thermal damage to the weld site during skin welding produces superior results. While cooling by passive thermal diffusion can be successful, there are advantages to active cooling of the tissue; the advantages and methods of active cooling are described below.

Figure 2:
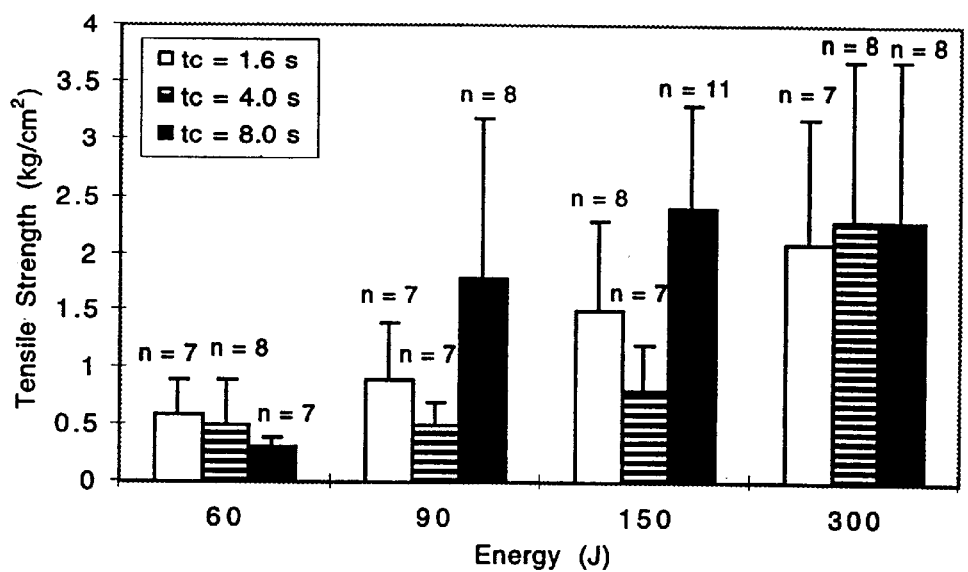
FIG. 2 is a graph showing the tensile strength of laser skin welds plotted as a function of total energy and cooling time between pulses. These studies were performed on skin, in vitro.

Multiple pulses of radiation are applied to the weld site until the tissue is closed and is found to demonstrate sufficient weld strength experimentally. This technique, when combined with a dye, allows thermal denaturation to accumulate selectively at the weld site, until the weld is completed. FIG. 2 also shows how weld strengths increase with cumulative energy delivered to the weld site, independent of cooling durations. These data are taken from laser skin welding studies performed in vitro.

If a laser is used as the radiation source, the laser spot size (i.e., the area irradiated by the incident laser radiation) should be large enough to allow simple alignment of the beam along the weld site. The spot size should also be large enough to allow the most uniform temperature distribution in depth into the tissue. In highly scattering tissue, a large spot size may be necessary to allow radiation to penetrate to the deeper layers of the tissue, and achieve a full-thickness weld. For example, skin is a highly scattering tissue. For welding skin that is approximately 2 mm in thickness, a large laser spot size should be used, on the order of 1–10 and preferably 1–6 mm in diameter.

Typically, the laser beam has a Gaussian profile. For tissue welding, however, it may be desirable to have a different beam profile. For example, a 'top-hat' beam profile may be used to provide a more uniform delivery of radiation to the weld site. Another possibility is to have two Gaussian beams or two top-hat beams side-by-side with a valley of minimum energy in the middle, corresponding to the site of the weld. Such a profile would limit absorption of radiation at the surface of the weld site, while allowing for heating of the subsurface layers of the weld site through scattering of radiation into the weld site from surrounding tissue. A beam profile with a minimum of energy at the surface of the weld could be produced by covering the surface of the weld site with a material that reflects the radiation. Alternatively, such a beam profile could be produced with two separate Gaussian or top-hat laser beams placed side by side.

EXOGENOUS ABSORBER

The second component of the invention is an exogenous absorber, such as a chromophore or dye that absorbs the radiation selectively, thus confining radiation absorption and the ensuing thermal denaturation to the immediate area of the weld site. This is an essential component of the welding system. It is not possible to perform tissue welding without an external absorber and still obtain both strong welds and limited thermal damage. For example, focusing the laser spot size down to a small area and using pulsed delivery of radiation in the absence of a dye, may confine heating of the tissue laterally, but the radiation will be either highly scattered or absorbed, such that minimal radiation reaches the deeper layers of the tissue. Such a technique would result in a weak, superficial weld, as described above.

If there is a desirable cosmetic result to be obtained, then the dye should not permanently tattoo the tissue to which it is applied. For tissue welding applications internal to the body, it may be acceptable to use an absorber that tattoos tissue, e.g. India ink, as long as the dye is not toxic. For example, Indocyanine Green (ICG) is a dye that is nontoxic, does not strongly tattoo, and is already approved for medical applications. ICG has an absorption peak at 810 nm when combined with albumin. This corresponds to a major wavelength of a commercially available diode laser. The ICG/diode laser combination thus represents one potential welding system. Other dye/laser combinations are obvious to those skilled in the art.

The exogenous absorber could be applied to the tissue in one of the following ways: The absorber could be applied directly to the wound edges with a syringe needle, micropipette, small applicator such as a cotton swab, or pre-dyed strip of paper or another polymeric material that is then removed or left in the weld site to biodegrade. For example, a strip of pre-dyed collagen-based material could be placed in the wound site to both simplify application of the dye and improve wound healing. Were the pre-dyed collagen-based material left at the weld site, then the preferred welding would be between the tissue proteins and the collagen-based material, with welding occurring to both sides of the collagen-based material. The absorber may be combined with an adhesive such as albumin or fibrinogen in a premixed solution to create a tissue "solder". Such a solder should provide easy and convenient use of the chromophore's absorption properties, should prevent decay or aggregation of the dye, and/or provide easier application to the tissue. For example, ICG can be mixed with albumin for stability. The albumin additionally acts as an adhesive and can promote wound healing and strength at the weld site. The exogenous absorber should not stain tissue lateral to the desired weld to a distance greater than the width of thermal confinement for a single pulse of radiation. This width will be determined by the amount of thermal damage that can be allowed without inhibiting the normal wound healing process. The thermal properties of the tissue determine the pulse duration necessary to achieve thermal confinement to the desired tissue region. Staining of tissue beyond the desired weld region will result in excessive thermal damage and inhibit wound healing. For example, during skin welding, radiation should be confined to within a distance of approximately 200 $\mu$m lateral to the weld site to prevent excessive thermal damage and delayed wound healing. Therefore, the dye should not stain the skin lateral to the weld site by more than 200 $\mu$m. It is also important that the staining of the tissue be as uniform as possible, so that the radiation is also absorbed uniformly along the dyed tissue.

The absorber should be applied to the tissue edges prior to closure, to form a full-thickness stained layer of the dye through the tissue. This application of the absorber is important so that radiation is absorbed only along the wound edges at the weld site. For example, the application of the absorber as a separate layer on top of the tissue surface would produce an undesirable weld: the radiation would be absorbed primarily at the surface of the tissue, not in the deeper layers of the tissue, thus producing more thermal damage at the tissue surface than is necessary, and a shallow, superficial weld with weak tensile strength. The temperature of the tissue along the apposed wound edges should reach about 50° C. to about 80° C.

TISSUE APPOSITION SYSTEM

The third component of the invention is a method for apposing the wound edges of the tissue together to produce intimate contact before and during welding. It is important that the cut edges of the proteins be brought into intimate contact uniformly along the weld site to allow for strong crosslinking of the proteins across the wound gap during welding. The degree of apposition of the tissue is vital to obtaining strong welds that consistently stay closed under tension.

The tissue apposition system may consist of a mechanical, biological, and/or chemical means of tissue closure. Mechanical methods of closure could be sutures, clips, staples, pins, or tapes. Biological glues could also be used, such as fibrinogen, fibrin sealant, albumin, or other blood product components. Chemical crosslinking agents could also be used such as cyanoacrylate glues, marine adhesives, gelatins, formaldehyde, glutaraldehyde, or hydroxyappatite cements for hard tissue applications. Any combination of the above methods of tissue apposition may be used so long as the apposition system does not mechanically or chemically interfere with the thermal bonding process.

TISSUE COOLING SYSTEM

The fourth and final component of the invention is a method of cooling the weld site and surrounding tissue between application of successive pulses. This component is necessary to minimize thermal damage in the upper layers of the tissue and in tissue lateral to the weld site. Passive cooling, as described above, can produce strong welds. Active cooling, however, may be necessary to reduce welding operation times and make laser welding more competitive with conventional tissue closure methods. In addition, there is evidence that rapid cooling of the weld site after welding may produce higher weld strengths than can be achieved during slower cooling.

Such a cooling system would cool the tissue at the weld site, as well as tissue immediately surrounding the weld site, to a temperature significantly below those temperatures that lead to thermal damage. If a large number of radiation pulses are applied to the tissue, then cooling should reduce the temperature of the immediate area of the weld site to approximately its initial pre-welding temperature, to prevent a buildup of the baseline temperature over time to a temperature above that of thermal denaturation temperatures.

Such cooling may take the form of natural cooling of the tissue through air convection, the application of water drip or spray, an ice pack, a cryogen spray, or a material with high thermal conductivity that when placed on the tissue surface or interstitially will draw thermal energy out of the tissue. The tissue may be cooled using any combination of these methods before, during, and/or after welding. The tissue may be cooled on the surface and/or in the subsurface layers.

DETAILED DESCRIPTION OF SKIN WELDING

In Vitro Examples

All experiments were performed in vitro using guinea pig skin. Adult female albino guinea pigs (Hartley, age 7–8 weeks, weight 400–500 g) were anesthetized with halothane, and then euthanized with an intravenous overdose of sodium pentobarbital. Animals were shaved and then epilated with a chemical depilator (Nair). The dorsal skin, including epidermis and dermis, was excised with a scalpel and sectioned into squares of approximately 3×3 cm. Tissue samples were then enclosed in a petri dish and preserved on a damp saline-soaked towel until used. All experiments were completed within 12 hours of tissue preparation.

A 2-cm-long, full-thickness incision was made in each skin sample with a #15 scalpel. All incisions were made parallel to the spine. Approximately 2–5 $\mu$l of India ink (Koh-I-Noor, 100 nm particle diameter) was then applied to the incision edges and into the wound with a micropipette. Excess dye was removed with a paper towel. Histologic analysis revealed that the dye penetrated 25–100 $\mu$m into the tissue. After the India ink dried, a thin layer of egg white (10% albumin) was applied to the incision edges as a temporary adhesive.

Welding was performed with a continuous wave Nd:YAG laser (Lee Laser, Model 703T) emitting radiation at a wavelength of 1.06 $\mu$m. The radiation was coupled into 600-$\mu$m core diameter silica optical fiber (3M) for flexible delivery. A 5-mm-diameter (FWHM) laser spot size was maintained during the experiments. The beam profile was approximately Gaussian. The power delivered to the tissue was kept constant at 10 W±0.2 W for all experiments. The output end of the fiber was scanned over the weld site using a stepper-motor-driven translation stage (Klinger Scientific Corp.) to simulate pulsed delivery of the radiation. The stepper motor was controlled by a personal computer (Hewlett Packard 386) that allowed programming of the scan velocity, cooling time between scans, and total number of scans. During welding, the velocity of the translator was kept constant at 47.6 mm/s, resulting in a pulse duration of ~100 ms, for the fixed 5-mm-diameter laser spot size.

The cooling time between scans was varied to study the difference between CW and pulsed welding. Three cooling times were selected: 1.6, 4.0, and 8.0 s. The cooling time is defined as the average time the laser beam takes to return to a particular 5 mm spot at the weld site during scanning. These times represent quasi-CW welding with minimal cooling, intermediate cooling, and long-duration cooling, respectively. Quasi-CW cooling was chosen to provide an estimation of the thermal damage achieved during CW welding, in which tissue temperatures are maintained above collagen denaturation thresholds for long periods of time. Intermediate cooling was studied in an attempt to allow the tissue to cool below denaturation temperatures between pulses, and to limit thermal damage to surrounding healthy tissue. Long-duration cooling was used to allow the temperature of the tissue to fall to approximately room temperature between pulses, and avoid buildup of the baseline temperature with successive pulses.

The energy delivered to the weld site was varied from 60 J to 300 J by changing the number of scans across the tissue. Each scan delivered 4.2 J of energy to the weld site. The total energy, E (J), incident on the surface of the 2-cm-long weld is $$E = \frac{p \times l \times s}{v}, \quad (2)$$

where p is power (10 W), l is weld length (20 mm), s is number of scans, and v is velocity (47.6 mm/sec). The total operation time ranged from 30 s to 10 min, depending on both inter-pulse cooling times and the total energy delivered to the weld site.

Upon completion of welding, the samples were placed in a covered petri dish onto a saline-soaked towel to preserve hydration of the tissue. Within 12 hours of tissue preparation, the samples were processed for either tensile strength measurements or histology. Table 4 provides a summary of the laser parameters used in this study.

TABLE 2

Summary of welding parameters.

| | |
|---|---|
| Animal Model: | albino guinea pig |
| Incision Length: | 2 cm full-thickness |
| Laser: | CW Nd:YAG |
| Wavelength: | 1.06 $\mu$m |
| Pulse Duration: | 100 ms |
| Cooling Time: | 1.6, 4.0, and 8.0 s |
| Repetition Rate: | 0.63, 0.25, 0.12 Hz |
| Power to Tissue: | 10.0 ± 0.2 W |
| Spot Diameter: | 5 mm (FWHM) |
| Total Energy: | 60–300 J |
| Operative Time: | 30 s - 10 min |
| Dye: | India ink |
| Absorption Coefficient: | 3500 cm$^{-1}$ |
| Adhesive: | egg white (10% albumin) |

FIG. 1 is a schematic of an apparatus which may be used for welding skin according to the subject invention.

Tensile strength of welded incisions was quantified using a tensiometer (MTS Sintech 20/G), with a 500 lb. load cell (±50 g accuracy). The length and thickness of each weld was measured before being tested. The tensiometer then pulled apart the weld at a rate of 6.35 mm/minute. A weld was judged as being broken as soon as a visible hole in the tissue could be seen at its weakest point. The breaking strength of the weld was divided by the weld length and thickness to arrive at a tensile strength (kg/cm$^2$). A minimum of 7 samples were tested for each set of laser parameters. Suture control studies were also performed. 5'0 Nylon sutures (Ethicon) were used to appose the 2-cm-long skin incisions. Either 1, 3, or 5 interrupted sutures were tied equidistant along the incision. The sutured wounds were also pulled apart using the tensiometer. Two suture strength values were recorded. The first value corresponded to when a hole could be seen in the tissue between the suture apposition points and represented the degree of tissue apposition. The second value was taken at the point at which the sutures failed. A minimum of 4 samples were tested for each set of parameters.

The thermal damage zone near the weld site was quantified following standard histologic preparation of tissue samples. A 4×4×2 mm sample of tissue was sectioned with a scalpel from the center of each completed weld, and stored in 10% formalin. Samples were processed in graded alcohols and xylines, paraffin embedded, sliced with a microtome, and stained with Hemotoxylin and Eosin dyes. A light microscope (Nikon) fit with crossed linear polarizers (Prinz) was used to analyze the sections. The boundary separating laser-denatured collagen from native collagen could be delineated based on the degree of collagen birefringence: native collagen transmitted light, while domains of denatured collagen did not. Thermal damage measurements were recorded at three different depths in the tissue, the epidermis, the middle of the dermis, and the bottom of the dermis, and measured laterally from the center of the weld site.

Statistical analyses were conducted on selected groups of data for weld and suture strengths and thermal damage measurements. ANOVA was used to determine statistical significance within and between data sets.

The parameters used in the in vitro study were selected based upon theoretical considerations.

A pulse duration of 100 ms was selected based on heat transfer theory. An approximate solution for the thermal relaxation time, $\tau_{Th}$, is given in equation 1.

For this application, the ~100 ms pulse duration used in these experiments was expected to yield an acceptable zone of thermal confinement of ~230 µm. It is important to note that equation 1 represents an approximate, order-of-magnitude estimate of thermal relaxation conditions, rather than an exact solution to the heat diffusion equation.

The tissue should cool down to about room temperature between scans to prevent baseline temperature rises with successive pulses. The rate of thermal diffusion is determined by the mass density, heat capacity, and thermal conductivity of the tissue being studied, as well as the geometry of the heat transfer problem. A conservative estimate for the time of temperature decay during the cooling phase, $\tau_c$, is on the order of 50–100 times the thermal relaxation time. By using suitably short pulses ($\tau_p < \tau_{Th}$) with sufficient cooling between pulses ($\tau_c > 100\tau_{Th}$) selective thermal damage to the weld site can be achieved without irreversibly damaging the tissue adjacent to the weld.

Welding was performed with near-infrared radiation that penetrates deeply into skin; thus uniform, full-thickness welds could be obtained. At near-IR wavelengths, scattering of radiation dominates absorption. Scattering of photons within the tissue can result in a significant decrease in penetration of the radiation and uniformity of the heating at deeper tissue depths. By using a large diameter beam, the radiation penetrates to the deeper layers of the tissue; thus, the temperature distribution is more uniform, and the welds should be stronger. Further, a large spot size allows easy alignment of the beam during welding. It is also probable that a high degree of scattering in the tissue aids the welding process by scattering a significant number of photons towards the dye layer at the weld site, where the photons are then absorbed.

India ink may be used for several reasons. First, an external absorber of radiation is necessary to selectively confine absorption of radiation to the immediate area of the weld site. Second, India ink is a much stronger absorber than other dyes used in welding. For example, Indocyanine Green (ICG), previously used with a diode laser for skin welding, has an extinction coefficient of $2 \times 10^5$ $M^{-1}cm^{-1}$ at 805 nm. If a concentration of 1 mg/ml of ICG is applied to skin, the absorption coefficient is ~600 $cm^{-1}$. Fluorescein Isothiocyanate, previously used with an argon laser for skin welding, has an extinction coefficient of $6 \times 10^4$ $M^{-1}cm^{-1}$ at 495 nm. If a concentration of 1 mg/ml is applied to skin, the absorption coefficient is ~350 $cm^{-1}$. The absorption coefficient of 100% India ink at 1.06 µm was measured to be approximately 3500 $cm^{-1}$. For comparison, assume an approximate absorption coefficient of $\mu_a = 0.3$ $cm^{-1}$ in skin at 1.06 µm. Thus, India ink serves as a very effective absorber of radiation that, when combined with pulsed delivery of radiation, can limit heating of the tissue to the immediate area of the weld site. Third, unlike other welding dyes, India ink absorbs strongly over a wide range of visible and IR wavelengths- There is no need to search for a laser with a wavelength that matches the absorption peak of the dye. Instead, one simply chooses a laser with a wavelength that has a deep penetration depth in tissue and allows for uniform, full-thickness heating of the weld site. Finally, India ink has a low toxicity when applied to skin, and is routinely used in the tattoo industry. The obvious disadvantage of using India ink is that the dye permanently tattoos the skin. Thus, the cosmetic result is less than desirable.

Weld strengths were recorded for three sets of cooling times and four sets of total energy, as shown in FIG. 2. The cooling durations, $\tau_c = 1.6$, 4.0, and 8.0 s, represent short, medium, and long-duration cooling between successive laser pulses, respectively. The total energy represents the total amount of energy supplied to the tissue along the 2-cm-long incision. For a fixed cooling time, the tensile strength of the weld increased with total energy delivered to the weld site. There is a clear difference in weld strengths when comparing the values for 60 J of energy and 300 J of energy, regardless of cooling time ($p<0.001$). The maximum weld strength was approximately 2.4 $kg/cm^2$, obtained with a cooling time of 8.0 s and a total energy of 150 J. A delivery of 300 J of energy for all three cooling times produced similar strengths. It is not clear whether weld strengths continue to increase for energy levels greater than 300 J, or plateau at a certain level. The study was terminated at 300 J, due to the large amount of thermal damage being seen at the weld site.

The tensile strength results show large standard deviations, sometimes as high as 60% of the weld strength. Such deviations can be attributed to errors in measurement, differences in tissue properties across samples, and perhaps most importantly, a technical inability to produce consistent apposition of tissue during closure prior to welding.

Figure 3:
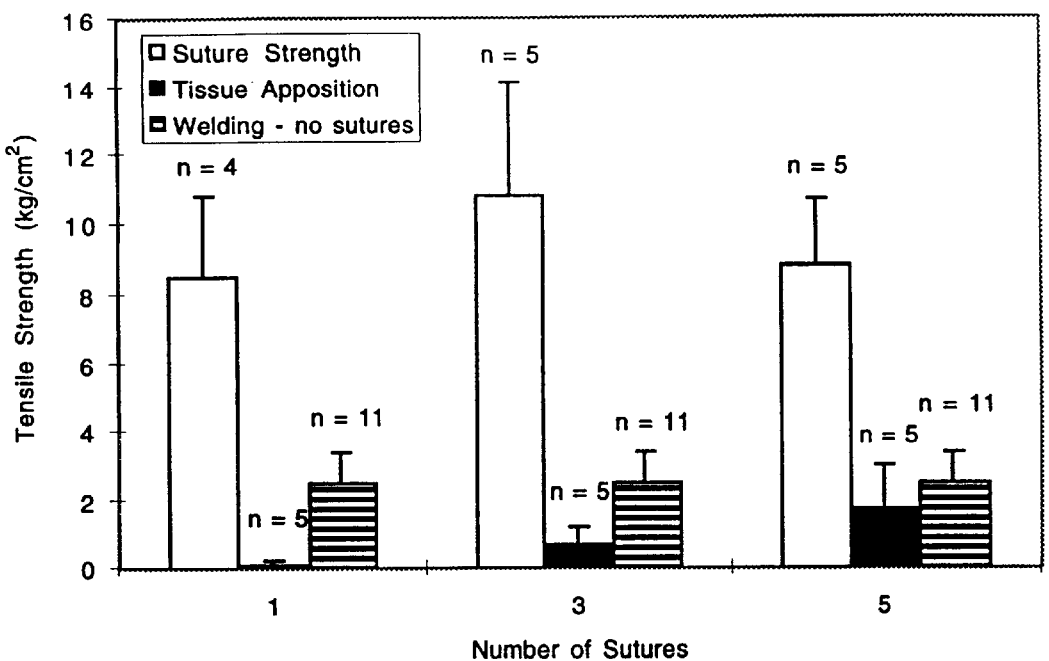
FIG. 3 is a graph showing the tensile strength of sutured wounds as a function of the number of sutures used to close the wounds.

The graph of FIG. 3 compares suture strengths with strengths obtained with the best laser parameters according to the subject invention. Tensile strength is plotted as a function of the number of interrupted sutures used per 2-cm-long incision. The left bar in each column represents the tensile strength of the sutures at their breaking point. This tensile strength is very large, roughly 8–11 $kg/cm^2$, and is statistically independent of the number of sutures used ($p>0.25$). The middle bar in each column represents the tissue apposition strength of the sutures, or the point at which the tissue opens up between sutures. Statistical analysis shows that the suture apposition strength increases with the number of sutures used to close the wound ($p<0.05$): as more sutures are applied to a wound of a fixed length, the distance between sutures decreases, and tissue apposition strength between suture points increases. All of the suture apposition strengths are below 2.0 $kg/cm^2$. The right bar in each column represents the best weld strength achieved with laser welding in the absence of sutures (150 J total energy and 8 s cooling between scans). It is present for comparison between laser weld strengths and suture strengths. FIG. 3 clearly indicates that while in vitro laser welded incisions are not as strong as sutured incisions, laser welded incisions have strength comparable to that at which tissue tears apart between suture points when 5 sutures are used ($p>0.25$).

It is generally recognized that if the lateral zone of thermal damage exceeds ~200 um into the tissue from the incision, then the wound healing process becomes delayed and excessive scarring occurs. FIG. 4 shows the differences of the thermal damage zones produced during both quasi-continuous wave and pulsed welding. Lateral thermal damage extending out from the weld site is plotted as a function of both total energy delivered and the cooling time between pulses. Four sets of total energy and three sets of inter-pulse cooling times were studied.

FIG. 4 demonstrates that within each data set, thermal damage at the epidermis is significantly greater than in the underlying dermal tissue ($p<0.05$). This is most likely due to a gradient in temperature from the top surface of the skin to the bottom surface. Both absorption and scattering of radiation contribute to this phenomenon.

Also, it can be seen that increasing the cooling time between laser pulses reduced the thermal damage at the weld site greatly. There is a statistically significant difference between epidermal thermal damage for welding with inter-pulse cooling times of 1.6 s and 8 s, for comparable energies (p<0.01). For comparable weld strengths of 2.0–2.4 kg/cm, quasi-CW welding (1.6 s of cooling between pulses) produced a zone of thermal damage of 2700±300 $\mu$m at the epidermis, while pulsed welding with a long cooling duration (8 s of cooling between pulses) produced only 500±150 $\mu$m of thermal damage. It is important to note that the thermal damage produced during true CW welding with no cooling would probably be greater than the 2700 $\mu$m measured for quasi-CW welding.

Weld strengths of 2.4 kg/cm$^2$ were measured using pulsed delivery of radiation. The immediate in vivo weld strength for skin is typically in the range of 0.15–0.50 kg/cm$^2$. Higher tensile strengths on the order of 1–2 k g/cm$^2$ have been published in the literature. In one of these studies, however, a $CO_2$ laser was used to weld skin, creating excessive thermal damage and poor wound healing. In the other study, both tape and sutures were used to facilitate wound apposition and strength.

Using the pulsed welding method of the subject invention, the middle and deeper layers of the dermis showed thermal damage zones less than 200 um in width. The thermal damage zone at the epidermis was also reduced significantly from 2700 $\mu$m to 500 $\mu$m by replacing CW welding with pulsed welding and long-duration cooling. There are several possibilities for reducing thermal damage even further. Cooling times longer than 8.0 s and/or pulse durations shorter than 100 ms may be necessary to provide for complete thermal relaxation in the tissue. It is also possible that thermal damage will be reduced in progressing from in vitro to in vivo welding studies due to increased hydration of the tissue, thus eliminating the need to refine the laser parameters.

In general, the typical thermal damage profile seen in the histology was cone shaped, with a large zone of thermal damage in the epidermis and upper layers of the dermis and less damage deeper within the dermis. This thermal damage profile demonstrates that even for deeply penetrating radiation at the 1.06-um wavelength, there is a substantial temperature gradient in the tissue. Absorption near the surface of the skin is high, resulting in higher temperatures and large amounts of thermal damage. Fewer photons penetrate into the deeper layers of the tissue, resulting in a smaller temperature rise and less thermal damage.

In evaluating the clinical value of laser welding, it is important to compare weld strengths with tissue apposition strengths as well as suture strengths. Although sutures provide strong closure of tissue, the wound actually opens up long before the sutures fail. The tissue gap between suture apposition points is an important indicator of wound healing because the wound is no longer watertight, and therefore serves as a potential site of infection. A perforation in the skin, if not properly sealed, will also result in the generation of scar tissue during the wound healing process. Our data indicate that in vitro weld strengths are comparable with the tissue apposition strengths achieved using 5 sutures to close a 2-cm-long incision.

An adhesive may be necessary to produce strong, reproducible welds. One of the goals of welding is to limit or eliminate the use of sutures in closing tissue. Weld strengths may depend greatly on the degree of apposition. Although egg white may serve as a simple temporary adhesive for in vitro work, other forms of adhesives may be necessary for in vivo application, where the weld is constantly under tension.

In Vivo Examples

The following examples demonstrate that the invention produces strong welds with thermal damage limited to the immediate area of the weld site. It can be seen that welds produced with limited thermal damage heal with no dehiscence and minimal histologically verifiable inflammation and scarring. Skin welding was performed using pulsed delivery of radiation in combination with a dye. By delivering the radiation to the weld site in a series of sufficiently short pulses, with adequate cooling between the pulses, cumulative thermal damage was confined to the immediate area of the weld site, while avoiding excessive thermal damage to surrounding healthy tissue. Strong welds were created with a zone of lateral thermal damage measuring only ~200 $\mu$m near the epidermis.

Adult female albino guinea pigs (age 7–8 weeks, weight 400–500 g, Harlan, Indianapolis, Ind.) were shaved then epilated with a chemical depilator (Nair, Carter-Wallace, New York, N.Y.). Each guinea pig was anesthetized with atropine (0.05 mg/kg), ketamine (30 mg/kg), and xylazine (2 mg/kg) administered by intraperitoneal injection. 1% lidocaine with 1:100,000 epinephrine was used as a local anesthetic at each incision site. The incision sites were then cleansed with antiseptic pads. Two-cm-long, full-thickness incisions were made parallel to the spine with a #15 scalpel. Four incisions were made on the back of each guinea pig. Two wounds were sealed using laser welding; the other two wounds were closed with sutures. From each of these two groups, one wound was taken for tensile strength testing and the other wound was processed for histologic analysis.

For the wounds that served as controls, three full-thickness, simple interrupted, 5'0 nylon sutures (Ethicon, Somerville, N.J.) were placed equidistant along each 2-cm-long incision. The wounds were then covered with an antibiotic ointment (Neosporin, Warner-Lambert, Morris Plains, N.J.) to prevent infection and desiccation of the wound. The ointment was applied twice daily for the first three days of wound healing. Sutures were removed 7 days post-operatively.

For the two incisions closed using laser welding, approximately 2–5 $\mu$l of India ink (Black India Rapidograph Ink, 3080-F, 100 nm particle diameter, Koh-I-Noor, Bloomsbury, N.J.) was applied to the wound edges and into the wound with a micropipette. The ink was allowed to dry, and excess ink was removed with cotton swabs. Histologic analysis revealed that the India ink diffused 20–50 [m into the skin from the incision edge. Controls performed using only sutures and India ink showed that the ink did not invoke an inflammatory response in the tissue.

The anesthetized animal was then placed prone on a translation stage. A mechanical clamping system was used to grip and push the wound edges together. The clamping system consisted of two grips made of a mesh of pins that were impressed upon the skin, but did not damage it. The grips were brought together to obtain tight, uniform apposition of the wound edges along the incision. Excess blood and fluid were removed from the wound site with cotton swabs prior to closure.

Welding was performed with a continuous-wave, Nd:YAG laser (Lee Laser, Model 703T, Orlando, Fla.) emitting radiation at a wavelength of 1.06 $\mu$m. The radiation was coupled into a 600-μm-core-diameter optical fiber (Thor Labs, Newton, N.J.) for flexible delivery. A 4-mm-diameter (FWHM) laser spot size was maintained during the experiments. The beam profile was approximately Gaussian. The laser spot size and beam profile were measured by scanning a 200-μm-diameter pin hole across the beam. The power emitted from the fiber was kept constant at 10.0±0.2 W. A stepper-motor-driven translation stage controlled by a personal computer was used to scan the 4-mm-diameter beam at a velocity of 47.6 mm/s producing ~80 ms pulses at each point along the incision so that the tissue along the wound edge reached 60° C. The cooling time between scans was held constant at 8 s. The cooling time is defined as the average time the laser beam takes to return to a particular point spot along the incision during scanning. Operation time was kept constant at 10 min per incision. The total energy delivered to each incision was approximately 315 J, delivered in 75 scans. Each scan delivered 4.2 J of total energy to the weld site. The radiant exposure at any particular point along the incision was 6.7 J/cm² per a scan. The total energy, E (J), incident on the surface of the 2-cm-length weld is $$E = \frac{p \times l \times s}{v}, \quad (3)$$

where p is power (10 W), l is weld length (20 mm), s is number of scans (75), and v is velocity (47.6 mm/sec). In order to minimize thermal damage to the skin outside the weld area, the beam was blocked with high-reflecting metal plates placed on each end of the incision.

FIG. 1 shows the experimental configuration used for dye-assisted laser skin welding. After welding, antibiotic ointment was not placed on the laser welds, due to concerns that the ointment would be absorbed into the weld site and affect bond strength.

Both tensile strength measurements and histologic analysis was performed on wounds closed by either laser or sutures at 0, 3, 6, 10, 14, 21, and 28 days post-operatively. On the appropriate day, the animal was anesthetized, and the dorsal skin, including epidermis and dermis, was excised with a scalpel and sectioned into squares of approximately 3×3 cm. The samples were then either taken for tensile strength testing or histologic processing.

All tensile strength tests were performed using a tensiometer (MTS, Sintech 20/G, Raleigh, N.C.) with a 500 lb. load cell (±50 g accuracy). The length of each weld was measured before being tested. All wounds had approximately the same thickness, ~2 mm. The tissue was gripped by clamps along the full width of the tissue on each side of the incision. The tensiometer then pulled normal to the axis of the incision at a rate of 6.35 mm/minute. An incision was judged as being broken as soon as a visible hole in the tissue could be seen at its weakest point. The breaking strength was recorded, and then divided by the length and thickness of the incision to arrive at a tensile strength in kg/cm². A minimum of three samples was tested at the end of each wound healing period.

Histologic analysis was performed on wounds closed by either laser or sutures at 0, 3, 6, 10, 14, 21, and 28 days post-operatively. A 4×4×2 mm sample of tissue was sectioned with a scalpel from the center of each incision, and stored in 10% formalin. Samples were processed using standard histologic techniques, including processing with graded alcohols and xylenes, parafin embedding, sectioning, and hemotoxylin and eosin staining. A minimum of three samples was taken at the end of each wound healing period.

A transmission light microscope (Nikon, Japan) fit with crossed linear polarizers (Prinz, Japan) was used to analyze the sections. Several quantitative indicators were used to compare wound healing among the laser weld and suture control groups. Birefringent images were used to measure thermal damage zones in welds processed immediately after surgery (Day 0). The boundary separating laser-denatured collagen from native collagen could be delineated based on the degree of collagen birefringence: native collagen transmitted light, while domains of denatured collagen did not. Thermal damage was measured laterally from the center of the weld site and recorded at three different depths in the tissue: the epidermis, the mid-dermis, and the deep dermis. Measurements were consistently taken at the demarcation point where complete birefringence loss was seen.

Epidermal thickness was also measured for both lasered and sutured wounds. The depth at which reepithelialization occurred, as well as the thickness of necrotic tissue sloughed during wound remodeling, was also recorded. Granulation tissue width measurements were performed at the epidermis, mid-dermis, and deep dermis. The amount of hair loss observed on the surface of the skin was recorded. Finally, photographs were taken of the skin surface 28 days after surgery to provide an image of the degree of apposition and cosmesis.

All survival animals were ambulatory within 1 hour following surgery and resumed their full range of normal activities without requiring special care. No dehiscence nor infection was noted in either laser welded or sutured wounds. Erythema was variably observed within the first millimeter immediately adjacent to the sutured and welded wounds. Typical signs of excessive irradiation of the weld site, such as blanching of the tissue, a rising of the tissue surface, and a hardening of the tissue at the weld site, were not observed post-operatively.

The tensile strength of wounds were measured for both laser welds and sutured wounds at 0, 3, 6, 10, 14, 21, and 28 days post-operatively. Immediate weld strengths of 2.1±0.7 kg/cm² were significantly higher than suture apposition strengths of 0.4±0.1 kg/cm² (p<0.01). However, after 3 days of wound healing, however, there was no statistical difference between weld and suture strengths (p>0.25). Both weld and suture strengths continued to increase over time, indicating a normal progression of the wound healing process.

The histological results showed that fill-thickness welds were not generally obtained during welding. Instead, welding occurred to a depth of only ~50% of the tissue thickness, or ~1 mm. As a result, the immediate weld strength values shown here for full-thickness, 2-mm-long welds were reported conservatively. The true strength of welds was approximately a factor of two greater than recorded here. Measured weld strengths would increase even further if full-thickness welds had been obtained.

In Vivo Sutured Incisions

Wounds closed with sutures appeared to follow the classical stages seen in healing by primary intention. After 3 days, wounds were typically closed from the mid-dermis and up, but remained open below the mid-dermis. Epidermal hyperplasia and migration of the epidermis beneath necrotic tissue was seen in all histologic sections. Rarely, complete bridging of the epidermis across the incision site was seen.

By day 6, sutured wounds were fully closed. Inflammatory cells were present at the wound site. Newly deposited collagen could be seen within a thin layer of granulation tissue that extended full-thickness through the skin. Reepithelialization was completed and the epidermal thickness had increased to ~280 μm. Near the epidermis, the granulation tissue measured 190 μm in width, but narrowed to a width of ~90 μm in the mid-dermis. At the base of the dermis, poor tissue apposition was probably a cause of the ~170 μm wide zone of granulation tissue.

At 10 days, the epidermis was 220 μm thick. As the epidermal hyperplasia decreased, some of the tissue volume was replaced with granulation tissue. The granulation tissue width near the epidermis measured ~330 μm after 10 days. From 14–28 days, wound healing continued in a normal manner (see FIGS. 3b and 3c). By 28 days, a full-thickness layer of granulation tissue could be seen, measuring less than ~100 μm in the upper layers near the epidermis, and narrowing to a fine scar width of approximately 80 μm and 60 μm in the mid- and deep dermis, respectively.

In Vivo Welded Incisions

Incisions closed with laser radiation followed a significantly different path of wound healing than those closed with sutures. The photothermal process of wound closure and the absence of suture apposition resulted in a varying degree of both tissue apposition and scar formation along the weld site. Images of wounds taken immediately after surgery showed a "funnel-shaped" zone of thermal damage. The average zone of thermal denaturation was 200 μm wide near the epidermis, decreasing to ~50 μm in the mid-dermis. The denaturation zone narrowed in the deeper layers of the skin and disappeared at a depth of ~1.0 mm. Thermal denaturation could not be seen in the deep dermis, where laser heating was apparently minimal. It can be concluded from these images, that full-thickness welds were not achieved. Instead, thermal denaturation extended only to a depth of ~50% of the skin thickness.

By day 3, a zone of thermally damaged necrotic tissue was present at the surface of the skin. The process of reepithelialization was in its earliest stages as the epidermis began to bridge under the denatured, desiccated, and necrotic surface tissue. Complete reepithelialization was not noted. In the deep layers of the dermis, the incision appeared torn apart, and new granulation tissue was filling the gap between the deep dermal wound edges. It appears that a combination of poor tissue apposition and the absence of thermal denaturation in the deep layers of the dermis resulted in the wound gap at the base of the dermis. The ink particles were deposited to a distance of ~1 mm laterally from the incision edge. Good tissue apposition, however, was present in the middle layers of the dermis where a moderate amount of thermal denaturation caused tissue bonding to occur without the formation of a large zone of necrotic tissue. The ink particles appeared to be spread out across a lateral distance of 100–250 μm of tissue, making measurement of the denatured tissue width difficult.

At 6 days the epidermis had hypertrophied to ~300 μm, and a complete epithelial bridge was present under necrotic tissue contained within a large thermal damage zone near the surface of the skin. The neo-epidermis bridged the wound gap at an average depth of ~400 μm. The necrotic tissue located in the region above the neo-epidermis and extending ~400 μm laterally from the weld site would eventually be sloughed during the subsequent stages of wound repair. A significant amount of thermally denatured tissue existed below the neo-epidermis. This thermal denaturation zone probably served as the source of the strength of the laser weld once the necrotic tissue above the epithelial bridge had been sloughed from the wound site, and prevented wound dehiscence from occurring during the early stages of wound remodeling. By day 10, the neo-epidermis had sloughed all of the necrotic tissue in the thermal damage zone above it. The epidermis had formed a complete and continuous layer across the surface of the skin, and epidermal hypertrophy had begun to disappear.

From day 14 through day 28, the wound healing process progressed. Beginning at between 14 and 21 days, a zone of granulation tissue, ~1 mm in thickness, appeared in the papillary dermis. This newly deposited granulation tissue filled the gap that was created after sloughing of thermally damaged tissue from the wound site, and during the recession in epidermal thickness. Several wound healing indicators, including epidermal thickness, width of granulation tissue, hair loss, and degree of tissue apposition, were used to make quantitative comparisons of wound healing progress between laser welds and sutured wounds. Measurements were not recorded until after 6 days, when reepithelialization bad been completed and a full epidermis was present. Normally, the epidermis is ~60 μm thick. After surgery, however, the epidermis hypertrophied to ~300 μm for both lasered and sutured incisions. No significant difference in epidermal thickness was found between laser and suture skin closure (p >0.25). The epidermis continued to decrease in thickness as wound healing progressed, and returned to a thickness of ~80 μm for both the laser and suture groups after 28 days.

The width of the granulation tissue for wounds closed with either laser or sutures was measured at the epidermis, the mid-dermis, and the base of the dermis, beginning after 6 days. For the laser welds, significant thermal damage in the papillary dermis resulted in a large zone of granulation tissue, ~500 μm thick by day 14. The granulation width in the papillary dermis increased to ~1 mm at 21 and 28 days, as the epidermis sloughed necrotic tissue from the wound site and began to recede in thickness. The granulation tissue width in the mid-dermis was relatively thin, due presumably to less thermal damage, and good tissue apposition. The extent of thermal denaturation was, however, difficult to measure quantitatively due to the presence of ink particles across a 200–400 μm zone. Near the base of the dermis, a large granulation tissue width was again present, due primarily to poor tissue apposition. The resulting wound gap filled in with granulation tissue, but the wide spread of ink particles across a 500–1000 μm area masked the amount of scar tissue present.

For the wounds closed with sutures, the granulation tissue width was significantly thinner than that detected in the laser welds, due presumably to both the absence of thermal damage, and better full-thickness tissue apposition. A relatively fine scar width was present through the full thickness of the tissue, measuring less than ~100 μm after 28 days.

The amount of hair loss at the surface of the skin was also measured for both laser welds and sutures after 28 days and used as an indicator of wound healing. Hair loss was measured laterally from the wound site at the surface of the skin. The average width of hair loss at the mid-point between the sutures was 0.9±0.3 mm (n=8), significantly less than the hair loss of 1.4±0.5 mm (n=8) measured for the laser welds (p<0.05). At the suture points, however, there was significantly more hair loss, 5.5±1.3 mm (n=8), than found along the laser welds (p<0.001).

Images of lasered and sutured wounds were taken at the end of each wound healing period. For the laser welded group, the tissue appeared to be more uniformly and consistently sealed along the entire 2-cm-long wound, during the early phase of wound healing. The sutured wounds, however, showed a large variation in tissue apposition during the first 6 days. Near suture points, the tissue was generally adequately apposed. Between sutures, however, a sloughing of wound edges was frequently observed. After 6 days, however, sutured wounds were typically fully closed, and poor tissue apposition was no longer observed.

It was difficult to make a quantitative comparison of the cosmetic appearance of lasered and sutured wounds at the end of the 28 day wound healing study. The sutured wounds typically showed a fine scar line, with some scarring still present at the suture marks. The scar line at the surface of the laser welds was not as noticeable, due to the presence of the India ink tattoo.

The results demonstrate that strong, viable welds can be achieved, in vivo, with less thermally induced tissue damage than reported in previous skin welding studies. Furthermore, the welds were created and endured without the aid of sutures, biological adhesives, or chemical cross-linking agents, and healed without dehiscence or excessive scarring in ambulatory animals. Welds were created with immediate tensile strengths higher than sutured wounds and weld strengths reported during previous skin welding studies. Weld strengths continued to increase over a period of 28 days, indicating the progression of normal wound healing.

Laser welding provides immediate weld strengths higher than sutures, since laser welding creates an immediate, uniform, and fluid-tight bonding of tissue across the wound site. Sutured tissue, however, is initially held together only at the suture points; between suture points, the immediate tensile strength is effectively zero.

Immediate weld strengths did not decrease when progressing from in vitro to in vivo experiments. The amount of fluid found at the weld site (e.g. blood, water), was much higher in vivo. Fluid was generally eliminated at the weld site, by actions such as adding epinephrine to the local anesthesia to act as a vasoconstrictor and reduce blood accumulation, and frequently toweling off remaining blood and other fluid from the weld site during preparation for welding. The weld site remained more hydrated, however, than in vitro experiments. The hydrated state of the tissue did not appear to have a significant effect on the in vivo results.

Acutely, in vivo weld strengths were $2.1 \pm 0.7$ kg/cm$^2$, comparable to observed in vitro weld strengths of $2.4 \pm 0.9$ kg/cm$^2$ ($p > 0.25$). If the weld thickness of the laser welds were determined by the depth of thermal denaturation (measured as ~1 mm), rather than the tissue thickness (measured as ~2 mm), then in vivo weld strengths were higher, $4.2 \pm 1.2$ kg/cm$^2$, than in vitro weld strengths.

During the 28 day wound healing period, weld and suture strengths were found to be comparable. The strength of laser welds continued to increase throughout the wound healing study, which indicates a relatively normal wound healing process.

The zone of thermal denaturation measured in vivo was significantly less than that measured during the in vitro work. This difference in thermal denaturation is due primarily to the laser parameters used for tissue welding. With CW delivery of radiation, heat diffusion from the weld site into surrounding tissue during welding produces a large zone of thermal damage. By the method of the subject invention radiation is delivered to the weld site in a series of sufficiently short pulses, with adequate cooling between the pulses, thereby thermally confining the absorbed energy to the immediate area of the weld site.

Histologic analysis revealed that thermal damage in the papillary dermis, combined with poor tissue apposition in the bottom layers of the dermis, resulted in significant granulation tissue formation. A "funnel-shaped" thermal damage profile was typically seen in the dermis. This thermal damage profile was most likely due to a temperature gradient in the tissue. It was expected that more 1.06-$\mu$m radiation would be absorbed by the dye in the epidermis and papillary dermis than in deeper structures. To counteract this tendency, a large laser spot size was used. Both experimental and theoretical results indicated that a larger irradiated area would yield deeper penetration of the radiation and fairly uniform, full-thickness denaturation along the wound edges.

Several signs indicated that wound healing of laser welds and sutures were comparable. There was no significant difference in epidermal thickness at any time during the 28 day study. No significant difference was found in the reepithelialization time for both the lasered and sutured incisions. There was also no major inflammatory response in the welds. Although histologic analysis showed greater scar formation in the laser welds than in the sutured wounds, surface photos of the welds revealed minimal scar formation. All of these observations indicate that laser welding does not result in delayed wound healing.

Spot Size and Beam Geometry

To achieve a strong weld throughout the thickness of the tissue one needs deep, uniform penetration of the incident radiation; thus, a large spot size should be used. Further, the laser parameters need to be chosen not only to denature tissue at the weld site deep within the dermis, but also to limit thermal damage near the surface of the tissue. By delivering the radiation in short pulses, with sufficient cooling between pulses, and using a large spot size, it should be possible to confine heating to the immediate area of the weld site throughout the full-thickness of the skin.

The use of a large spot size in welding applications serves several purposes. Thermal damage can be achieved in the deeper layers of the dermis through direct absorption of radiation, rather than by diffusion of thermal energy that might be absorbed more shallowly, thus providing more uniform heating of the weld site. The use of a large spot size also makes easier alignment of the laser beam along the incision during welding.

The following examples compare laser spot diameters of 1, 2, 4, and 6 mm (FWHM), with laser output powers of 1, 4, 16, and 36 W, respectively. The beam profile for all spot diameters was approximately Gaussian. The laser spot size and beam profile were measured by scanning a 200-$\mu$m-diameter pin hole across the beam. The power delivered to the tissue was monitored by a power meter (Molectron PowerMax 5100, Portland, Oreg.). The irradiance remained constant at 127 W/cm$^2$ for each spot size. The total energy delivered to the weld site was 140, 280, 560, and 840 J for the 1, 2, 4, and 6 mm spot sizes, respectively. The total energy delivered to the weld site during an individual scan was 2, 4, 8, and 12 J, respectively. In order to minimize thermal damage to the skin outside the weld area, the beam was blocked with high-reflecting metal plates placed on each end of the incision. Table 3 summarizes the laser parameters for this study.

TABLE 3

Summary of laser parameters

| Spot (mm) | N | Power (W) | Total Energy (J) |
|---|---|---|---|
| 1 | 7 | 1.0 | 140 |
| 2 | 7 | 4.0 | 280 |
| 4 | 7 | 16.0 | 560 |
| 6 | 2 | 36.0 | 840 |

Figure 5:
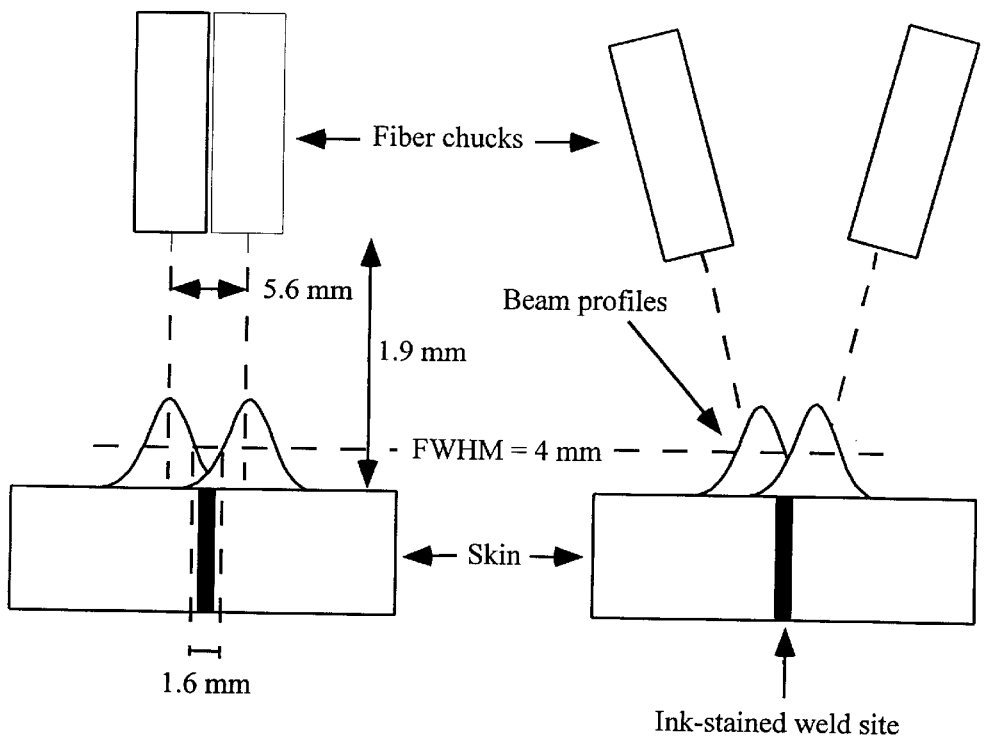
FIGS. 5A and 5B shows a laser beam profile study for dual beam experiments.

The following examples used a beamsplitter to couple radiation equally into two separate fibers. Two approximately Gaussian beams, each with an output power of 8 W and 4 mm laser spot diameter, were placed next to each other, forming a double peak with a valley in between (FIGS. 5a and 5b). The minima of this beam profile was aligned along the weld site during welding. This beam profile was used in an attempt to limit radiation absorption at the surface of the skin, and produce subsurface thermal damage through scattering of photons into the ink-stained weld site.

FIGS. 5a and 5b represent two different possible laser beam profiles for dual beam welding. The following laser parameters were held constant. Power was 8 W out of each fiber, and the laser spot size was 4 mm (FWHM) at the tissue surface for each fiber. In FIG. 5a, the laser beam profile is shown as a pair of only slightly overlapping Gaussian beams with center irradiance at ½ the maximum irradiance of each outer peak. In FIG. 5b, the laser beams overlap more than in FIG. 5a; thus, the beam has an irradiance that is slightly less along the weld than lateral to the weld and the diameter of the beam is ~8 mm. The results of this experiment showed the typical "funnel-shaped" thermal damage profile seen in the single-beam experiments, but with poorer tissue apposition at the surface, and less depth of thermal damage.

Immediately following laser welding, the anesthetized guinea pig was euthanized with an intracardiac overdose of sodium pentobarbital (Nembutal, Abbott Laboratories, North Chicago, Ill.). The dorsal skin, including epidermis and dermis, was excised with a scalpel and samples were then taken for histologic processing. Samples were processed using standard histological techniques, including storage in 10% formalin, processing with graded alcohols and xylenes, parafin embedding, sectioning, and hemotoxylin and eosin staining. A minimum of 7 samples were processed for each laser spot size and geometry. The 6-mm-diameter spot study was discontinued due to concerns over animal welfare after grossly obvious burns developed at the wound site.

Thermal damage measurements were made on the welds processed immediately after surgery using a transmission light microscope (Nikon, Japan) fit with crossed linear polarizers (Prinz, Japan). Thermal denaturation was measured laterally from the center of the weld site at three different depths in the tissue: the epidermis, mid-dermis, and base of the dermis. The depth of thermal damage was also recorded and divided by the tissue thickness to obtain the fraction of a fill-thickness weld that was achieved. Thermal damage measurements were consistently taken at the point at which complete thermal denaturation of the tissue was observed.

The results of the laser spot size study are shown in Table 4. The average thickness of all the samples was 1900±200 $\mu$m. Shallow welds were achieved using a 1-mm-diameter laser spot, measuring only 570±100 $\mu$m in average depth, or ~30% dermal thickness. Thermal denaturation was observed only in the upper layers of the dermis. Although lateral thermal damage was limited to only 100±30 $\mu$m near the surface of the tissue, the superficial depth of the welds resulted in weak strength. The majority of the welds processed in this spot size group fell apart either immediately after surgery or during the histological processing of the tissue samples. The weld appears open in the middle and lower layers of the dermis due to poor tissue apposition, absence of thermal denaturation, and/or tearing caused during histological processing.

TABLE 4

The effect of laser spot size on the thermal damage profile.

| Spot Diam (mm) | Lateral Thermal Damage ($\mu$m) | | | Depth ($\mu$m) | % Thickness |
|---|---|---|---|---|---|
| | Papillary Dermis | Mid-Dermis | Deep Dermis | | |
| 1 | 100 ± 30 | 0 | 0 | 570 ± 100 | 30 ± 6 |
| 2 | 240 ± 40 | 70 ± 25 | 0 | 970 ± 210 | 51 ± 10 |
| 4 | 240 ± 50 | 150 ± 40 | 0 | 1470 ± 190 | 80 ± 7 |
| 6 | ~450 | ~200 | ~150 | ~1900 | 100 |

When the laser spot diameter was increased to 2 mm, thermal denaturation was observed in the middle layers of the dermis. The thermal denaturation extended to an average depth of 970±210 $\mu$m, or ~50% thickness of the dermis. This depth was significantly greater than achieved with a 1-mm-diameter spot (p<0.001). The weld is open in the bottom layers of the dermis due to an absence of thermally denatured tissue. Significantly more lateral thermal damage was also measured at the surface of the skin, ~240±40 $\mu$m (p<0.001). The welds appeared, qualitatively, to be stronger than those observed in the 1-mm-diameter spot studies.

Increasing the spot diameter to 4 mm resulted in welds with an average depth of 1470±190 $\mu$m, or ~80% dermal thickness. The depth of these welds was significantly greater than that produced in both the 1-mm- and 2-mm-diameter spot studies (p<0.001). Lateral thermal damage near the epidermis measured 240±50 $\mu$m, similar to that measured for the 2-mm-diameter spot study p>0.25). Significantly more thermal denaturation was measured in the middle layers of the dermis for the 4-mm-diameter spot (150±40 $\mu$m) than for the 2-mm-diameter spot (70±25 $\mu$m) (p<0.01). The thermal denaturation gradient was less, however, when moving from the upper to middle layers of the dermis for the 4-mm-diameter spot than for the 2-mm-diameter spot. The use of a larger laser spot size resulted in not only deeper, but also more uniform welds. These welds appeared to be relatively strong and did not fall apart during welding nor afterwards during processing for histology.

Experiments performed with a 6-mm-diameter spot resulted in full-thickness welds of 1900 $\mu$m in depth. During surgery, however, the tissue surrounding the weld site began to redden, blanch, and eventually burn. These experiments were terminated before statistically significant quantitative data could be obtained, due to concerns over the welfare of the animals.

Experiments were also performed using a dual Gaussian beam and a laser spot diameter of 4 mm, with 8 W output from each fiber. Attempts to limit thermal damage at the surface of the skin by scattering radiation into the subsurface layers of the ink-stained weld site from the side proved to be unsuccessful. The tissue typically remained open at the surface with stepping between the tissue edges. The thermal denaturation gradient, however, remained similar to that of single beam studies, with the majority of denaturation seen in the top layers of the skin. Attempts to move the fibers further apart resulted in a disappearance of all thermal damage and complete absence of welding.

Several important observations were made during this study. First, increasing the laser spot size resulted in a significant increase in the thermal denaturation depth achieved at the weld site. As a general rule, the laser spot diameter should be much larger than the tissue thickness to obtain the deepest and most uniform welds. With small diameter laser spots, it is only possible to achieve deep denaturation of skin with a long pulse duration (e.g. continuous-wave mode) and diffusion of heat to the deeper tissue, rather than through direct absorption of the radiation. The problem with CW welding is that significant lateral thermal damage will also occur around the weld site. It is therefore believed that using a large diameter laser spot that results in the deepest thermal denaturation of tissue, while minimizing lateral thermal denaturation, will also result in the thickest welds. Fuller-thickness welds should result in higher tensile strengths with less probability of dehiscence and minimal scarring during wound healing.

Second, our data suggest that for the given laser parameters, there may be an optimum laser spot size of between 4–6 mm in diameter. Welding with a laser spot diameter of 4 mm or less resulted in welds that are less than full-thickness. Welding at larger diameter laser spots of 6 mm or greater, however, resulted in both excessive lateral thermal damage and the development of burns for radiance of 127 W/cm$^2$.

Active Cooling

Figure 6:
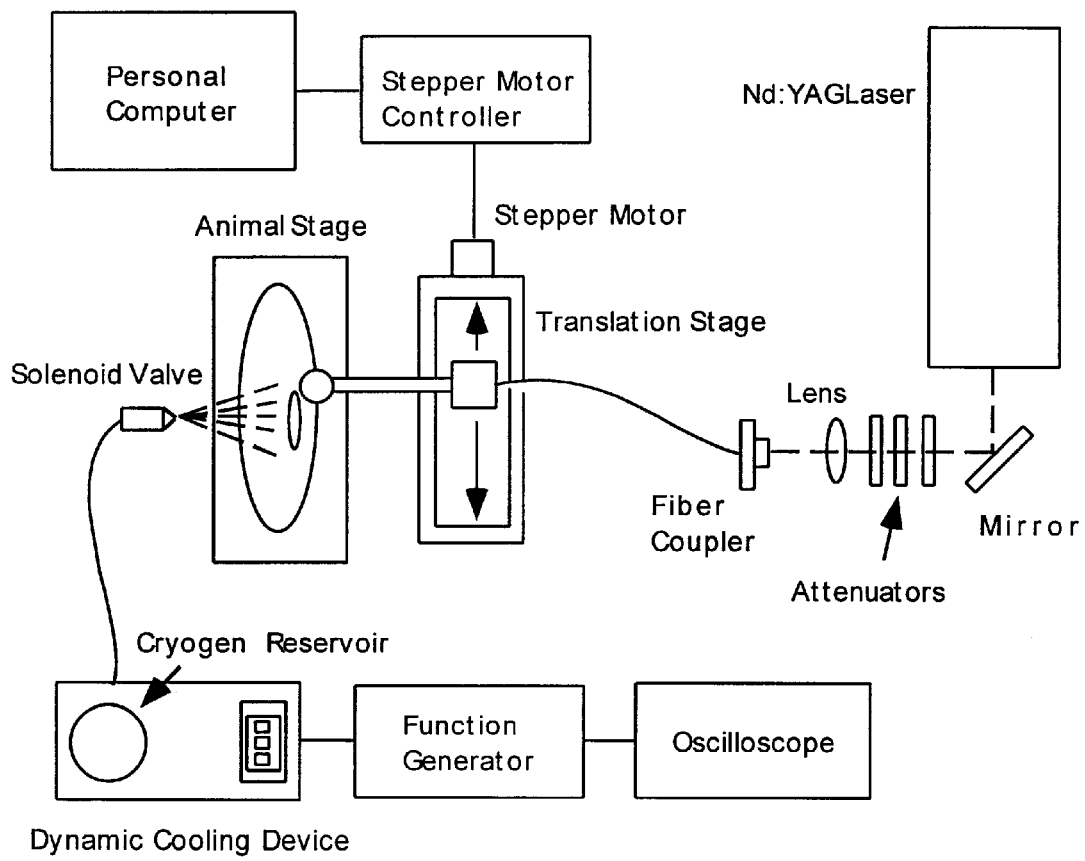
FIG. 6 is a schematic showing the cryogenic cooling during the laser skin welding of the subject invention.

In addition, in order to minimize further the thermal damage to the skin at the surface of the weld area Dynamic Cooling Device (DCD) (Candela Corporation, Wayland, Mass.) was used to deliver the cryogen (Halocarbon 134a, 1,1,1,2-Tetrafluoroethane, BP=−26° C., Candela Corporation, Wayland, Mass.) to the weld site through a solenoid valve (Parker General Valve Division, Fairfield, N.J.) in spurt durations of 20, 60, or 100 ms. The time between spurts was either 2 or 4 s. The working distance from the solenoid valve to the tissue surface was held constant at 12 ±1 cm, with the spray covering an area of approximately 5 cm×5 cm. FIG. 6 shows the experimental configuration used for cryogen cooling during laser skin welding.

Following the procedure, each animal was euthanized. The dorsal skin was then excised, and the welds were taken either for tensile testing or processed for histologic analysis. For each set of irradiation and cooling parameters, a minimum of three welds were selected for either histological analysis or tensile strength measurements.

The tensile strength of welded incisions was quantified using a tensiometer (MTS Sintech 20/G, Raleigh, N.C.), with a 500 lb. load cell (±50 g accuracy). The length and thickness of each weld was measured before being tested. The tissue was gripped by clamps along the fill width of the tissue on each side of the weld. The tensiometer then pulled normal to the axis of the weld at a rate of 6.35 mm/min. A weld was judged as being broken as soon as a visible hole in the tissue could be seen at its weakest point. The breaking strength of the weld was divided by the weld length and thickness to arrive at a tensile strength (kg/cm$^2$).

For the histologic studies, a 4×4×2 mm tissue sample was sectioned with a scalpel from the center of each wound site. Samples were processed using standard histologic techniques, including storage in 10% formalin, processing with graded alcohols and xylenes, parafin embedding, sectioning, and hemotoxylin and eosin staining. Thermal denaturation was measured laterally from the center of the weld site and recorded at three different depths in the tissue: the epidermis, the mid-dermis, and the deep dermis. Both light microscopy and polarized light microscopy were used to determine the extent of thermal damage.

For the first and second groups, in which relatively high cooling repetition rates of 0.50 Hz were used, the weld strengths were very weak. At the short, 20 ms cooling durations, weld strengths remained below 1.0 kg/cm$^2$. For the intermediate, 60 ms cooling durations, the weld strengths were effectively zero, due to the accumulation of water on the surface of the welds. Likewise, for the long, 100 ms cooling durations, strengths were effectively zero due to the buildup of frost on the skin surface. Only the welds performed with relatively low cooling repetition rates of 0.25 Hz, demonstrated high tensile strengths. Weld strengths ranged from 1.3–2.1 kg/cm$^2$, with no statistically significant difference among the data (p>0.05).

The first cooling group shows less than 200 μm of denaturation at the epidermis. Denaturation in the dermis exceeded 500 μm except, however, for long cooling durations of 100 ms, in which deep dermal denaturation was not obtained. For the second cooling group, the energy deposition was increased, resulting in a corresponding increase in the extent of denaturation throughout the tissue. Deep dermal denaturation was still not achieved, however, using 100-ms-long cooling durations.

In the third and fourth cooling groups, the cooling repetition rate was decreased to 0.25 Hz, resulting in a larger denaturation zone. Only the measurements recorded for an energy deposition of 252 J, cooling repetition rate of 0.25 Hz, and cooling duration of 100 ms showed thermal denaturation zones that were not excessive. The lateral thermal denaturation zone at the epidermis, mid-dermis, and deep dermis measured 320±80 μm, 430±90 μm, and 220 μm, respectively. These parameters also produced tensile strengths of 1.7±0.4 kg/cm$^2$. All of the other data groups produced either weak tensile strengths or excessive thermal denaturation zones. Table 5 provides a summary of the tensile strength and thermal damage measurements under the condition of 1.06-micron radiation delivered via an optical fiber irradiating a 4 mm diameter region scanned at 38.1 mm/s to achieve ~100 ms -long pulses at a radiant exposure of 13.4 J/cm$^2$ with the total number of scans varied from 10 to 60 to vary the total energy delivered from 84 to 504 J.

TABLE 5

Summary of Results for Welding with Cryogen Spray Cooling.

| Parameters | Tensile Strength | Thermal Damage | Visual Indicators |
| --- | --- | --- | --- |
| Controls | | | |
| 84 J | Low | Low | None |
| 168 J | Low | Very High | BK, B, R, RD |
| 252 J | Low | Very High | BK, B, R, RD |
| 252 J, 0.50 Hz, 20 ms | Low | Low | RD |
| 252 J, 0.50 Hz, 60 ms | None | Very Low | W |
| 252 J, 0.50 Hz, 100 ms | None | Very Low | F |
| 504 J, 0.50 Hz, 20 ms | Low | Intermediate | R |
| 504 J, 0.50 Hz, 60 ms | None | Low | W |
| 504 J, 0.50 Hz, 100 ms | None | Very Low | F |
| 252 J, 0.25 Hz, 20 ms | High | High | BK, B, R, RD |
| 252 J, 0.25 Hz, 60 ms | Intermediate | Intermediate | R, RD |

TABLE 5-continued

Summary of Results for Welding with Cryogen Spray Cooling.

| Parameters | Tensile Strength | Thermal Damage | Visual Indicators |
|---|---|---|---|
| 252 J, 0.25 Hz, 100 ms | High | Low | None |
| 504 J, 0.25 Hz, 20 ms | Very High | Very High | BK, B, R, RD |
| 504 J, 0.25 Hz, 60 ms | High | High | BK, B, R, RD |
| 504 J, 0.25 Hz, 100 ms | High | Very High | R |

The results demonstrate that the application of a cryogen coolant to the skin surface during tissue welding can allow denaturation of the weld site in the deeper layers of the skin, while decreasing the thermal denaturation zone near the surface. The goal is to create strong, full-thickness welds and minimize the thermal denaturation at the weld site. In practice, however, one has to balance these two goals. Too much thermal denaturation will result in high immediate tensile strengths that then decrease during wound healing, as the thermally damaged tissue is sloughed from the weld site. Dehiscence and excessive scarring may then occur. Too little thermal denaturation may result in weak welds that dehisce immediately after surgery, when under tension.

For this study, the best set of parameters required the delivery of 252 J of total energy (13.4 J/cm$^2$) to the weld site during an operation time of 1 min. Cryogen was applied to the surface of the skin only once every two scans, or at a repetition rate of 0.25 Hz. The cooling durations, however, were relatively long at 100 ms. These parameters produced welds with average tensile strengths of 1.7±0.4 kg/cm$^2$ (mean±S.D., n=4). Lateral thermal damage, measured 320±80 μm, 430±90 μm, and 220 μm, at the epidermis, mid-dermis, and deep dermis, respectively.

In summary, the preferred embodiment of the invention involves in vivo localized welding of tissue which is achieved by 1) applying an absorbing material (e.g. a dye) along the edges of the wound, throughout the depth of the wound, 2) apposing the dyed edges of the wound and 3) irradiating the wound with laser radiation that deeply penetrates the wound and is absorbed by the absorbing material at the apposed wound edges. The radiation should have pulses less than 250 ms in duration, with sufficient cooling (either active or passive) between pulses to prevent thermal damage to surrounding healthy tissue, and with a sufficiently large irradiated area (1–10 mm in diameter) to achieve thermal denaturation along the apposed edges of the wound, throughout the depth of the wound. The energy in each pulse must be sufficient to raise the temperature at the wound edges to greater than the threshold denaturation temperature of the tissue proteins. Thus, the radiant exposures should be between 1–100 J/cm$^2$, preferably 1–25 J/cm$^2$. The total energy deposited must be such that the cumulative denaturation leads to a strong weld. Thus, 20–500 pulses, preferably 40–200 pulses are required.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

What is claimed is:

1. A method of welding tissue wounds, including the sequential steps of:
   a) Applying an exogenous absorber material to the wound along the wound edges and throughout the depth of the wound;
   b) Apposing the wound edges of the tissue:
   c) Irradiating the wound in a pulsed mode of pulses of about 80 ms to about 250 ms so as to confine the irradiated energy to an immediate area surrounding the wound, the energy of about 1 to about 100 J/cm$^2$ to weld the tissue edges together; and
   d) cooling the immediate area for a period of over 1 sec after each said pulse during irradiation.

2. The method of claim 1, wherein said exogenous absorber material is a dye, chromophore or pigment that absorbs the incident energy more strongly than the native tissue absorbs the incident energy.

3. The method of claim 1, wherein said exogenous absorber material is India ink.

4. The method of claim 1, wherein said exogenous absorber material is Indocyanine Green.

5. The method of claim 1, wherein the wound edges are apposed by a chemical, mechanical or physical means.

6. The method of claim 1, wherein the wound edges are apposed by egg white.

7. The method of claim 1, wherein the step of irradiating the wound is performed with a laser.

8. The method of claim 7, wherein said laser irradiates a region of 4–6 mm in diameter.

9. The method of claim 7 wherein said laser radiant exposure is between about 1–25 J/cm.

10. The method of claim 7, wherein the laser emits radiation at a wavelength between 650 to 1300 nm.

11. The method of claim 7, wherein the time between laser pulses is sufficient to prevent thermal damage to surrounding healthy tissue.

12. A method of healing tissue wounds, consisting essentially of the steps of:
   a) Applying an exogenous absorber material selected from the group consisting of a dye, a chromophome and pigment into a wound area throughout the depth of the wound;
   b) Apposing the wound edges of the tissue;
   c) Irradiating the wound area with a laser beam, in a pulsed mode with pulses of up to about 250 ms so as to confine the laser beam to an immediate area surrounding the wound, with energy of about 1 to about 100 J/cm$^2$ to weld the tissue edges together; and
   d) cooling the wound area during irradiation.

13. The method of claim 12, wherein between laser pulses the wound area cools for 20 ms to 10 s and the laser beam has an irradiance of 10–200 W/cm$^2$.

14. The method of claim 12, wherein the laser beam has a scan velocity of greater than 15 mm/sec.

15. The method of claim 12, wherein the laser beam has a scan velocity of 50 mm/sec.

16. A method of welding tissue wounds, including the sequential steps of:
   a) Applying an exogenous absorber material to the wound along the wound edges;

b) Apposing the wound edges of the tissue;

c) Irradiating the wound in a pulsed mode so as to confine the irradiated energy to an immediate area surrounding the wound, with sufficient energy to weld the tissue edges together whereby the incident radiation is provided via a beam with maximal lateral to the weld site and a minimum at the surface of the weld; and d) cooling the immediate area during irradiation.

17. The method of claim 16, wherein the beam consists of two top-hat regions with no energy incident on the weld surface.

18. The method of claim 16, wherein the beam consists of two Gaussian regions with no energy incident on the weld surface.

19. A method of welding tissue wounds, including the sequential steps of:

a) Applying an exogenous absorber material to the wound along the wound edges;

b) Apposing the wound edges of the tissue with egg white;

c) irradiating the wound in a pulsed mode so as to confine the irradiated energy to an immediate area surrounding the wound, with sufficient energy to weld the tissue edges together, d) cooling the immediate area during irradiation.

* * * * *